(12) United States Patent
Bootwala et al.

(10) Patent No.: US 9,918,755 B2
(45) Date of Patent: Mar. 20, 2018

(54) IMPLANT DISPENSER

(71) Applicant: DePuy Synthes Products, Inc., Raynham, MA (US)

(72) Inventors: Zoher Bootwala, West Chester, PA (US); Sean Saidha, West Chester, PA (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 125 days.

(21) Appl. No.: 14/754,139

(22) Filed: Jun. 29, 2015

(65) Prior Publication Data

US 2016/0374737 A1    Dec. 29, 2016

(51) Int. Cl.
  *A61B 17/70* (2006.01)
  *A61B 17/00* (2006.01)

(52) U.S. Cl.
  CPC ........ *A61B 17/7091* (2013.01); *A61B 17/708* (2013.01); *A61B 17/7044* (2013.01); *A61B 17/7074* (2013.01); *A61B 17/7082* (2013.01); *A61B 2017/00398* (2013.01); *A61B 2017/00862* (2013.01)

(58) Field of Classification Search
  CPC .................. A61B 17/7091; A61B 17/7082
  See application file for complete search history.

(56) References Cited

U.S. PATENT DOCUMENTS

| | | |
|---|---|---|
| 2,247,500 A | 7/1941 | Hutchison, Jr. |
| 2,868,053 A | 1/1959 | Jorgensen et al. |
| 3,971,421 A | 7/1976 | Damratowski |
| 4,018,254 A | 4/1977 | DeCaro |
| 5,167,174 A | 12/1992 | Fujiyama et al. |
| 5,339,713 A | 8/1994 | Hou |
| 5,445,641 A | 8/1995 | Frigg et al. |
| 5,791,207 A | 8/1998 | Ahdoot |
| 5,957,927 A | 9/1999 | Magee et al. |
| 6,328,746 B1 | 12/2001 | Gambale |
| 6,595,998 B2 | 7/2003 | Johnson et al. |
| 6,676,001 B1 | 1/2004 | Chen et al. |
| 6,701,811 B1 | 3/2004 | Chang et al. |

(Continued)

FOREIGN PATENT DOCUMENTS

WO    2008/097974    8/2008

OTHER PUBLICATIONS

European Search Report (EP 12167870.0); dated Jul. 20, 2012.

*Primary Examiner* — Jacqueline Johanas
(74) *Attorney, Agent, or Firm* — Dunlap Codding, P.C.

(57) ABSTRACT

An apparatus for dispensing a plurality of implants including a barrel, a magazine, and a driver. The barrel has a longitudinal passage and a lateral passage intersecting the longitudinal passage adjacent a distal end of the barrel. The magazine has a housing defining a chamber for holding a plurality of implants. The housing is slidably connected to the barrel and movable between a retracted position and an extended position wherein a slot of the housing is aligned with the lateral passage of the barrel. A pusher member connected to the housing is caused to push one of the implants through the slot and the lateral passage and into the longitudinal passage. The driver is disposed in the longitudinal passage to be axially and rotatably movable to apply a rotational force to the implant.

20 Claims, 18 Drawing Sheets

(56) References Cited

U.S. PATENT DOCUMENTS

| | | | |
|---|---|---|---|
| 6,997,929 B2 * | 2/2006 | Manzi | A61B 17/025 606/90 |
| 7,461,574 B2 | 12/2008 | Lewis et al. | |
| 7,481,813 B1 | 1/2009 | Purcell | |
| 7,691,129 B2 | 4/2010 | Felix | |
| 7,717,921 B2 | 5/2010 | Rezach | |
| 7,722,623 B2 | 5/2010 | Franks et al. | |
| 7,753,912 B2 * | 7/2010 | Raymond | A61B 17/8852 606/90 |
| 8,105,328 B2 | 1/2012 | Protopsaltis | |
| 8,282,651 B2 | 10/2012 | Ciccone et al. | |
| 8,403,933 B2 | 3/2013 | Rutledge | |
| 8,998,958 B2 | 4/2015 | Dauster et al. | |
| 9,439,783 B2 * | 9/2016 | McLean | A61F 2/4611 |
| 2003/0225408 A1 | 12/2003 | Nichols et al. | |
| 2004/0243139 A1 * | 12/2004 | Lewis | A61B 17/862 606/104 |
| 2005/0149031 A1 * | 7/2005 | Ciccone | A61B 17/1615 606/280 |
| 2006/0036244 A1 | 2/2006 | Spitler et al. | |
| 2006/0229629 A1 * | 10/2006 | Manzi | A61B 17/025 606/90 |
| 2007/0093849 A1 | 4/2007 | Jones et al. | |
| 2007/0213722 A1 | 9/2007 | Jones et al. | |
| 2008/0154278 A1 | 6/2008 | Abdelgany | |
| 2008/0255576 A1 | 10/2008 | Protopsaltis | |
| 2008/0264218 A1 | 10/2008 | Wang et al. | |
| 2009/0163962 A1 | 6/2009 | Dauster et al. | |
| 2011/0040335 A1 | 2/2011 | Stihl et al. | |
| 2012/0290012 A1 | 11/2012 | Rutledge | |
| 2014/0046333 A1 * | 2/2014 | Johnson | A61B 17/025 606/90 |
| 2014/0277476 A1 * | 9/2014 | McLean | A61F 2/442 623/17.16 |
| 2015/0105831 A1 | 4/2015 | Yim et al. | |

* cited by examiner

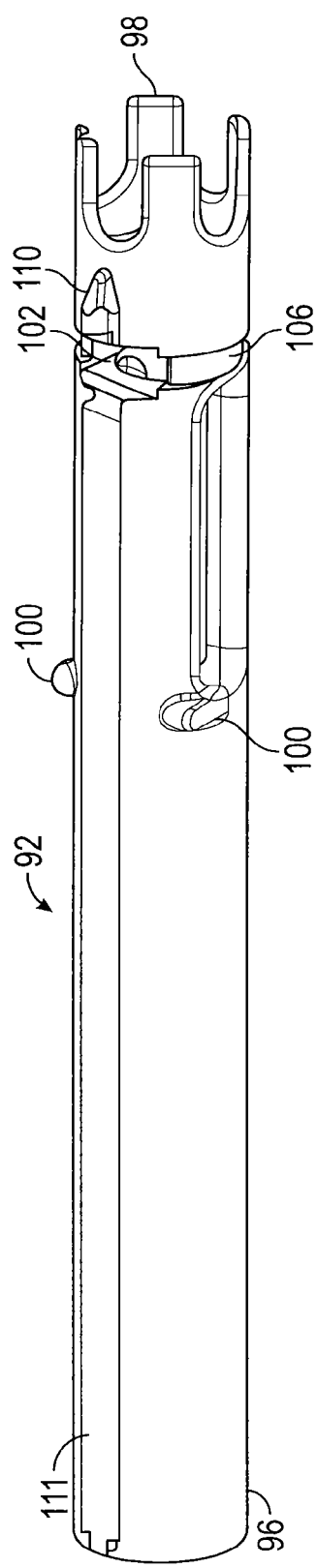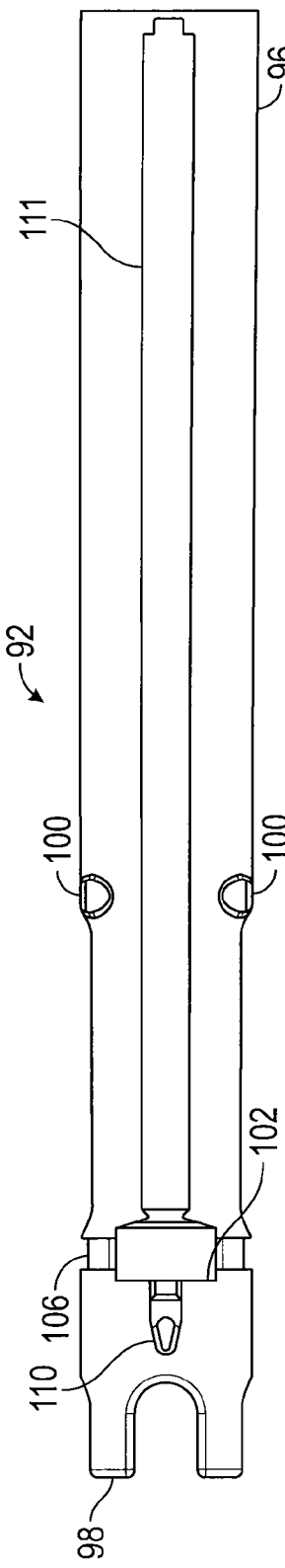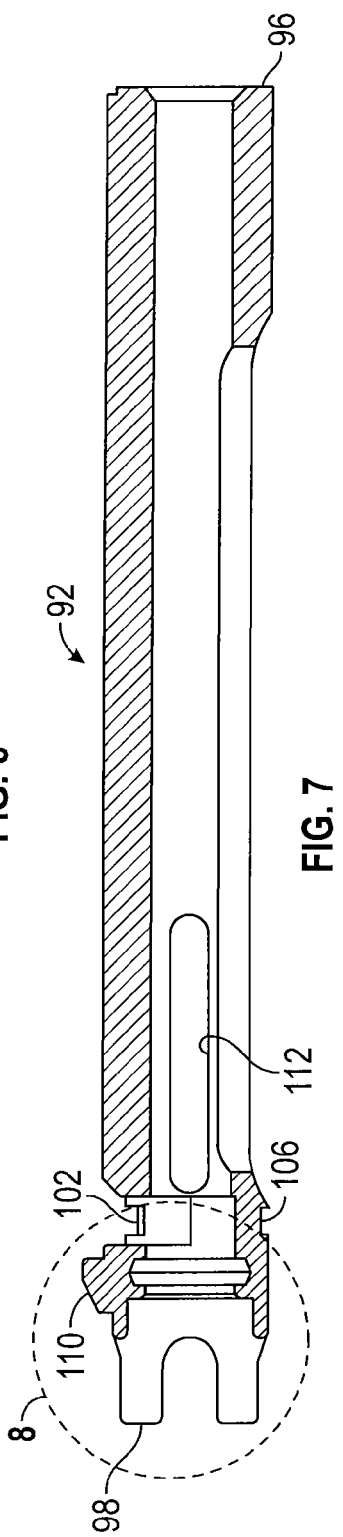

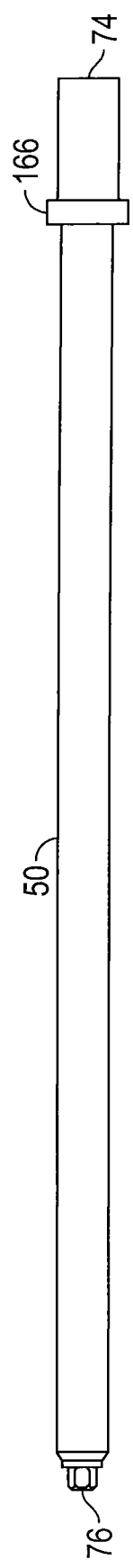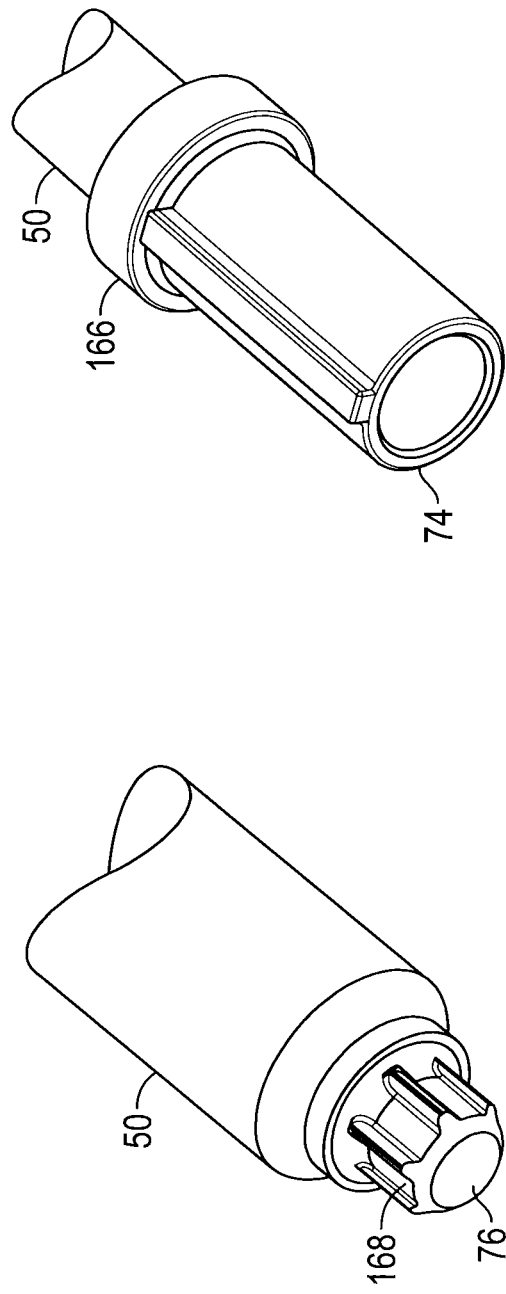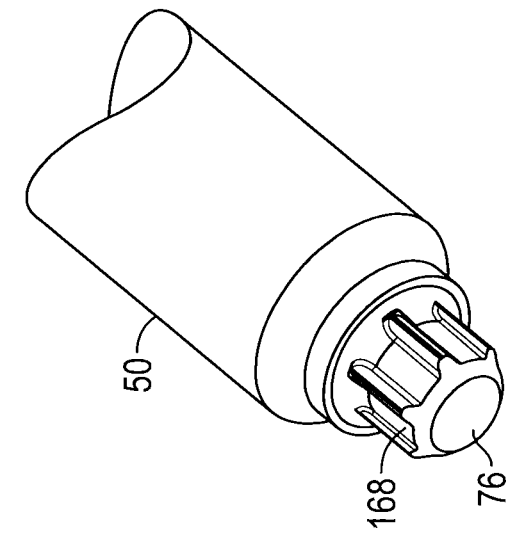
FIG. 19
FIG. 20B
FIG. 20A it may protrude from the instrument. The protrusion caused by the plate or cartridge in turn prevents the practitioner from having a clear view of the rod receiving head. This in turn causes the practitioner to have a more difficult time applying the locking cap to the rod receiving head.

To this end, a need exists for an improved apparatus and method for delivering multiple implants, such as locking caps, while allowing for a more clear view and minimizing the time associated with handling and tightening such implants during surgery. It is to such an apparatus and method that the inventive concepts disclosed and claimed herein are directed.

IMPLANT DISPENSER

BACKGROUND

Several techniques and systems have been developed for correcting and stabilizing the spine and for facilitating fusion at various levels of the spine. Stabilization of the spine for various conditions, such as degenerative disk disease, scoliosis, spondylolisthesis, and spinal stenosis, to name a few, often require attaching implants to the spine and then securing the implants to spinal rods. Such spinal fixation devices can immobilize the vertebrae of the spine and can alter the alignment of the spine over a large number of vertebrae by connecting at least one elongate rod to the sequence of selected vertebrae. These rods can span a large number of vertebrae, such as three or four. The spine anatomy, however, rarely allows for three or more implants to be directly in line. In order to allow for this irregularity, the rod must be contoured to the coronal and lateral planes.

Spinal fixation has become a common approach in fusion of vertebrae and treating fractures and the above listed spinal disorders. A common device used for spinal fixation is a bone fixation plate assembly. Typical bone fixation plate assemblies have a relatively flat, rectangular plate with a plurality of apertures therethrough. Another option is an implantation fixation system that locks a rod to several vertebrae. In these systems, as with other spinal fixation systems, various fasteners, such as bone screws and spacers, are used to secure the implantation fixation assembly to the desired and targeted vertebrae of the patient. These screws vary in design and shape, depending upon their desired location and use.

Screws, such as polyaxial, monoaxial, and uniaxial screws, are frequently used as fasteners in implantation fixation systems. Once these screws are set in a desired position, the screws are securely fixed in that position to minimize or eliminate movement of the vertebra. This is typically accomplished with a fixation system that securely engages the screw.

There are numerous screws and fixation systems existing in the market today. Some fixation systems utilize a rod receiving head having a central passage and a screw inserted into the central passage. The screw has a head portion that seats inside one end of the rod receiving head, and a threaded shank that projects through the end of the rod receiving head in an exposed manner. An elongated rod is seated in the rod receiving head and extends transversely through the central passage. The rod is secured in the rod receiving head with an implant commonly known as a locking cap that is screwed around the exterior of the rod receiving head or in the interior of the rod receiving head to lock the rod in place.

Locking caps are typically inserted into the rod receiving head with an instrument that has been loaded with a single locking cap. Consequently, after one locking cap is threaded into the rod receiving head with the instrument, a surgeon is handed another instrument loaded with another locking cap, or the same instrument is passed to a technician who loads the same instrument with another locking cap and passes back to the surgeon. The application of the locking caps continues in this back and forth fashion until all the locking caps are threaded and secured into position, and thus the application of the locking caps is a time consuming process.

Some practitioners have attempted to alleviate this problem by allowing for loading of multiple locking caps into an instrument via a plate or cartridge containing the multiple caps. While this instrument may expedite the application of locking caps onto a rod receiving head, the plate or cartridge

BRIEF DESCRIPTION OF THE DRAWINGS

FIG. 5 is a perspective view of a barrel base of the implant dispenser.

FIG. 6 is a top plan view of the barrel base of FIG. 5.

FIG. 7 is a sectional view of the barrel base of FIG. 5.

FIG. 19 is a side elevational view of a driver.

FIG. 20A is a perspective view of a distal end of the driver of FIG. 19.

FIG. 20B is a perspective view of a proximal end of the driver of FIG. 19.

DETAILED DESCRIPTION OF EXEMPLARY EMBODIMENTS

Figure 1:
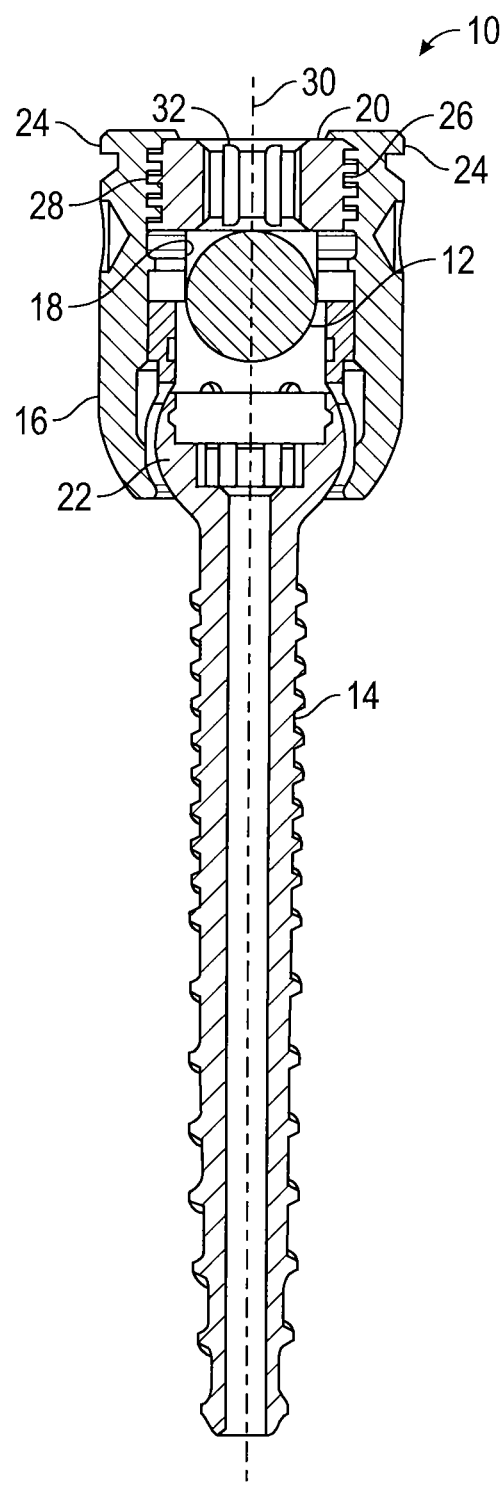
FIG. 1 is a sectional view of a prior art bone fixation element including a implant.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments, or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having," and any variations thereof, are intended to cover a non-exclusive inclusion. For example, a process, method, article, or apparatus that comprises a list of elements is not necessarily limited to only those elements, and may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B is true (or present).

In addition, use of the "a" or "an" are employed to describe elements and components of the embodiments disclosed herein. This is done merely for convenience and to give a general sense of the inventive concepts. This description should be read to include one or at least one and the singular also includes the plural unless it is obvious that it is meant otherwise.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the drawings, FIG. 1 illustrates an exemplary embodiment of a bone fixation element 10 for use in a posterior spinal fixation procedure to interconnect a longitudinal rod 12 with a patient's vertebra. Broadly, the bone fixation element 10 includes a bone anchor 14 for securing the bone fixation element 10 to a patient's vertebra, a rod receiving head 16 having a rod-receiving channel 18 for receiving the rod 12, and an implant 20, commonly known as a locking cap, for securing the rod 12 in the rod-receiving channel 18 in an implanted configuration. The bone anchor 14 is shown to include an enlarged head portion 22 which is received within an inner spherical cavity formed in rod receiving head 16 so that the bone anchor 14 can poly-axial rotate with respect to the rod receiving head 16. Alternatively, the bone anchor 14 may be formed integral with the rod receiving head 16 to form a monolithic structure which is referred to as a mono-axial pedicle screw or hook.

The rod receiving head 16 has a pair of arms 24 which define the rod receiving chamber 18. The arms 24 include a plurality of threads 26 on an inner surface thereof for threadably receiving the implant 20.

The implant 20 is shown to be in the form of a one piece implant including a plurality of external threads 28 threadingly engageable to the plurality of threads 26 on the inner surface of the arms 24 and an internal bored 30 defined by a plurality of internal ridges 32

Exemplary embodiments of pedicle screws include those described in International Patent Application No. PCT/US2008/070670, filed on Jul. 21, 2008, entitled "Polyaxial Bone Fixation Element," International Patent Application No. PCT/US2006/015692, filed on Apr. 25, 2006, entitled "Bone Anchor with Locking Cap and Method of Spinal Fixation," and International Patent Application No. PCT/CH1997/00236, filed on Jun. 16, 1997, entitled "Device for Connecting a Longitudinal Support with a Pedicle Screw," the contents of which are hereby incorporated by reference in their entirety. It should be understood, however, that the inventive concepts disclosed herein are is not limited in use to any particular type of implant or pedicle screw. By way of example, the inventive concepts disclosed herein may be used to dispense other types of implants, such as pedicle screws and set screws, by way of example.

As described above, the process of securing the implants 20 to the rod receiving head 16 can be a tedious and time consuming process. To this end, a need exists for an improved apparatus and method for delivering multiple implants.

Figure 2A:
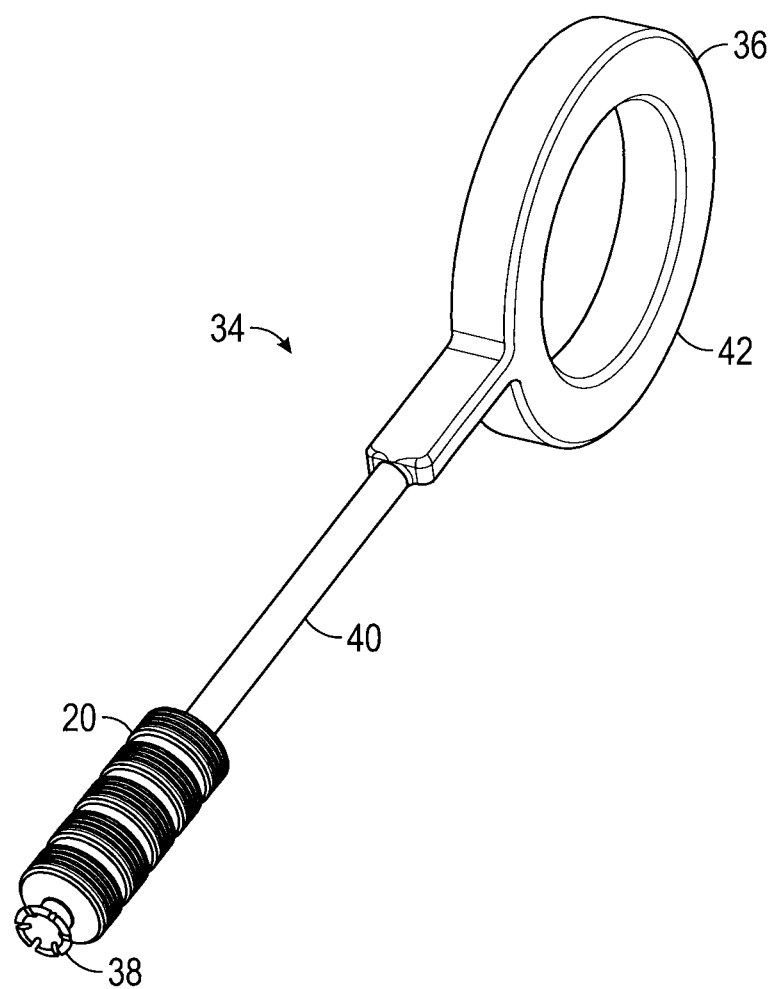
FIG. 2A is a perspective view of an implant string with a plurality of implants disposed thereon in accordance with one illustrative embodiment.
Figure 2B:
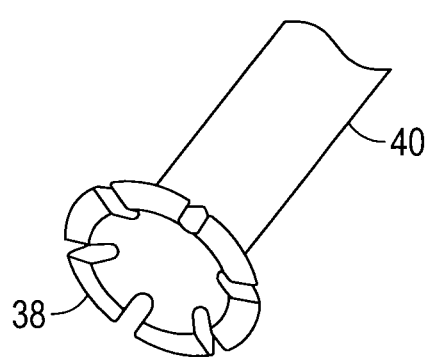
FIG. 2B is a partial, perspective view of a distal end of the implant string of FIG. 2A.

Referring now to the illustrative embodiment of FIGS. 2A and 2B, an implant string 34 is configured to support a plurality of implants, such as implants 20. The implant string 34 has a proximal end 36, a distal end 38, and an elongated portion 40 for holding the implants 20. The proximal end 36 of the implant string 34 has a loop 42 sized such that a human finger may be disposed into the loop 42. As is more clearly shown in FIG. 2B, the distal end 38 of the implant string 34 is flared and flexible in such a way that allows the implants 20 to be retained on the elongated portion 40 of the implant string 34, but allows the implant string 34 to be withdrawn from the plurality of implants 20. The elongated portion 40 of the implant string 34 has sufficient length to hold a plurality of implants 20. Use of the implant string 34 will be described below.

Figure 3:
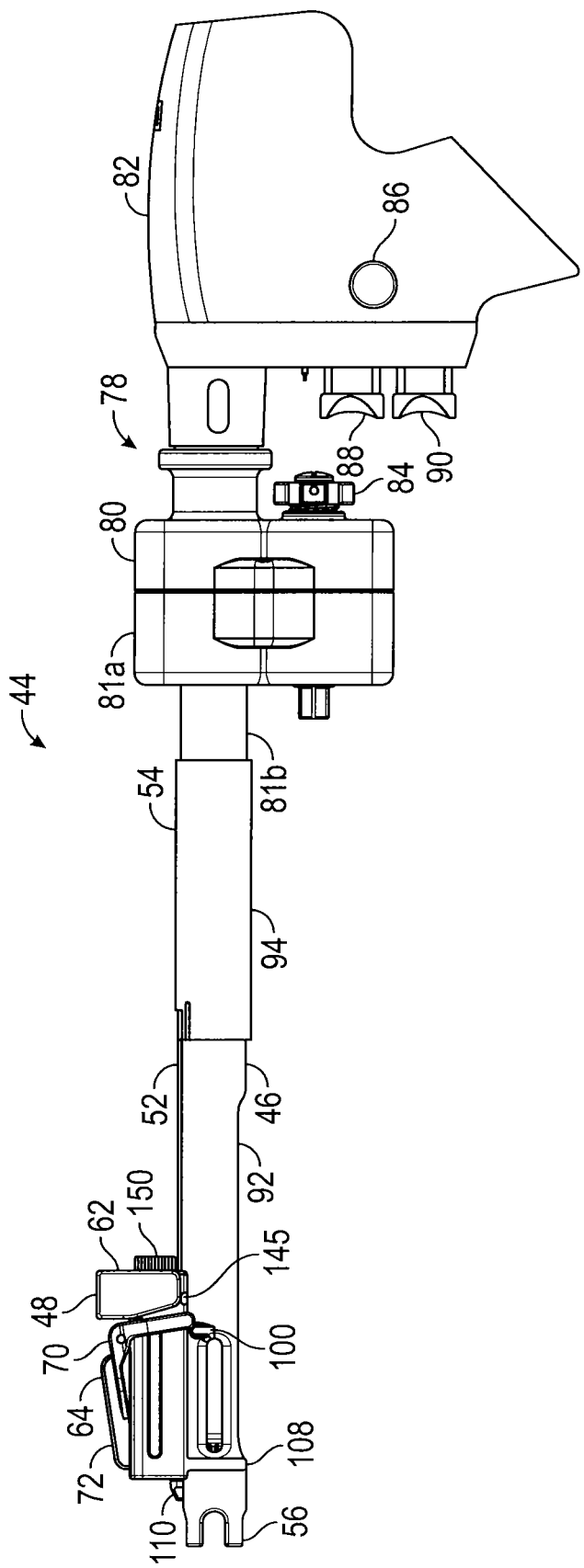
FIG. 3 is a side elevational view of an implant dispenser constructed in accordance with one illustrative embodiment of the inventive concepts disclosed herein.
Figure 4:
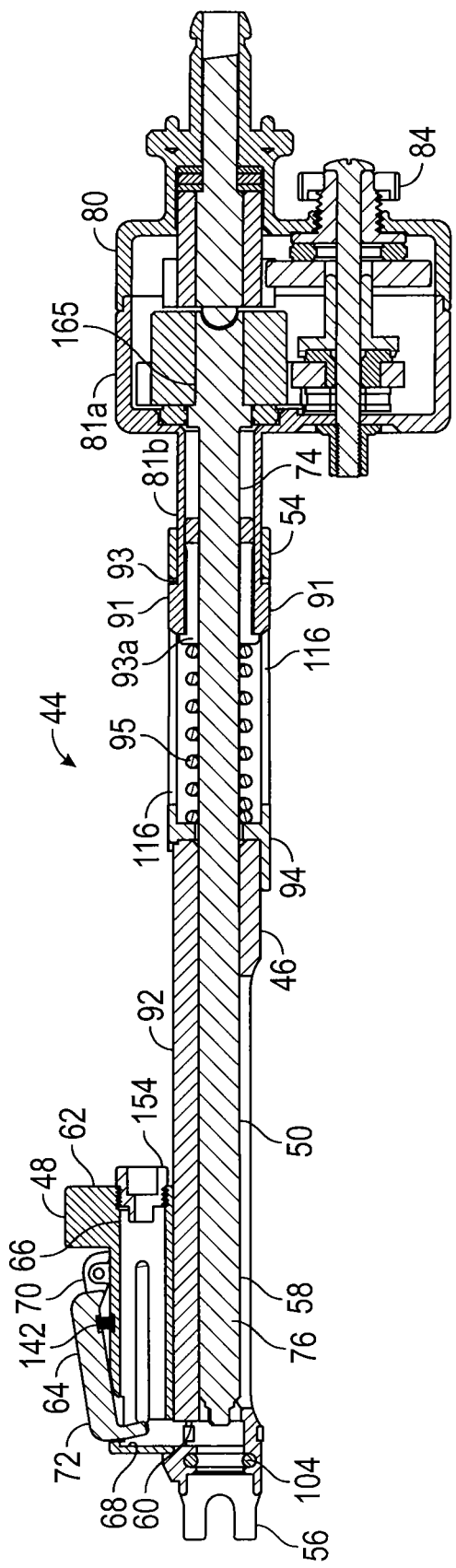
FIG. 4 is a sectional view of the implant dispenser.
Figure 8:
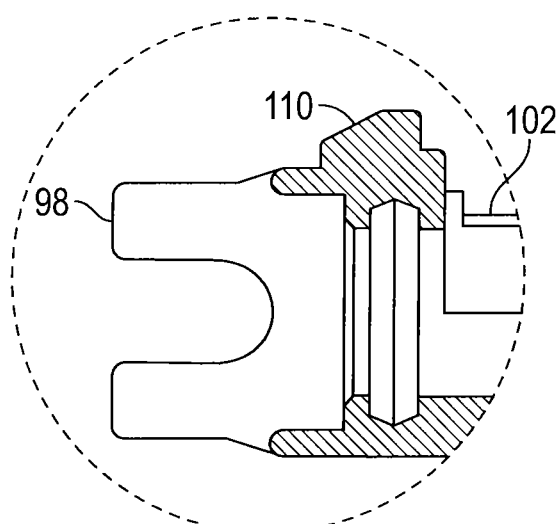
FIG. 8 is an enlarged sectional view of the barrel base of FIG. 5.
Figure 9:
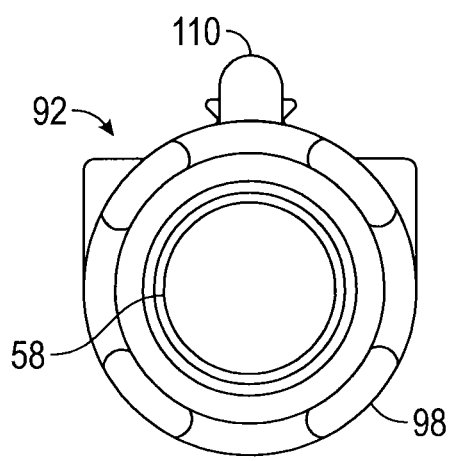
FIG. 9 is an end view of the barrel base of FIG. 5.
Figure 10:
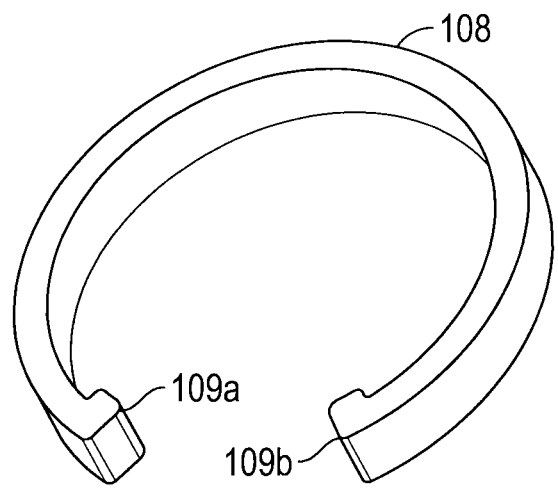
FIG. 10 is a perspective view of a snap ring of the implant dispenser.
Figure 27A:
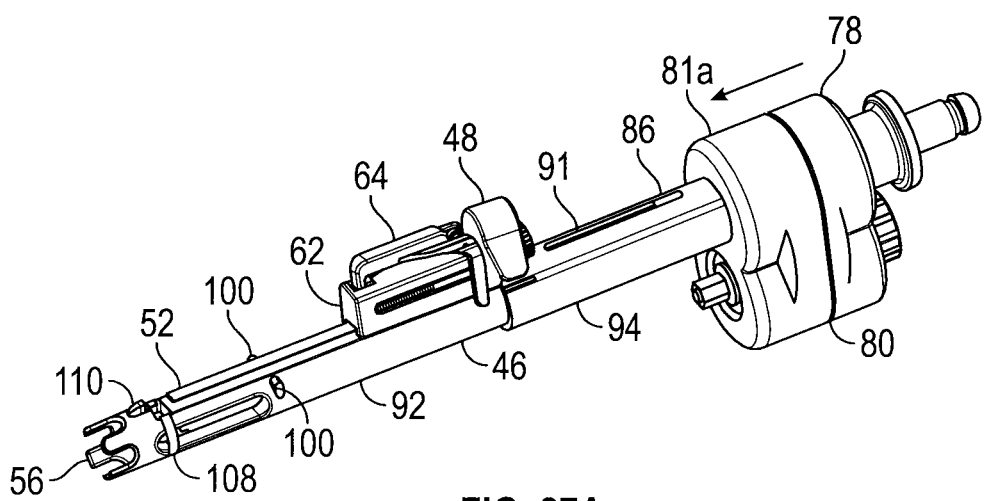
FIG. 27A is a perspective view of the implant dispenser shown with the driver in an extended position.
Figure 27B:
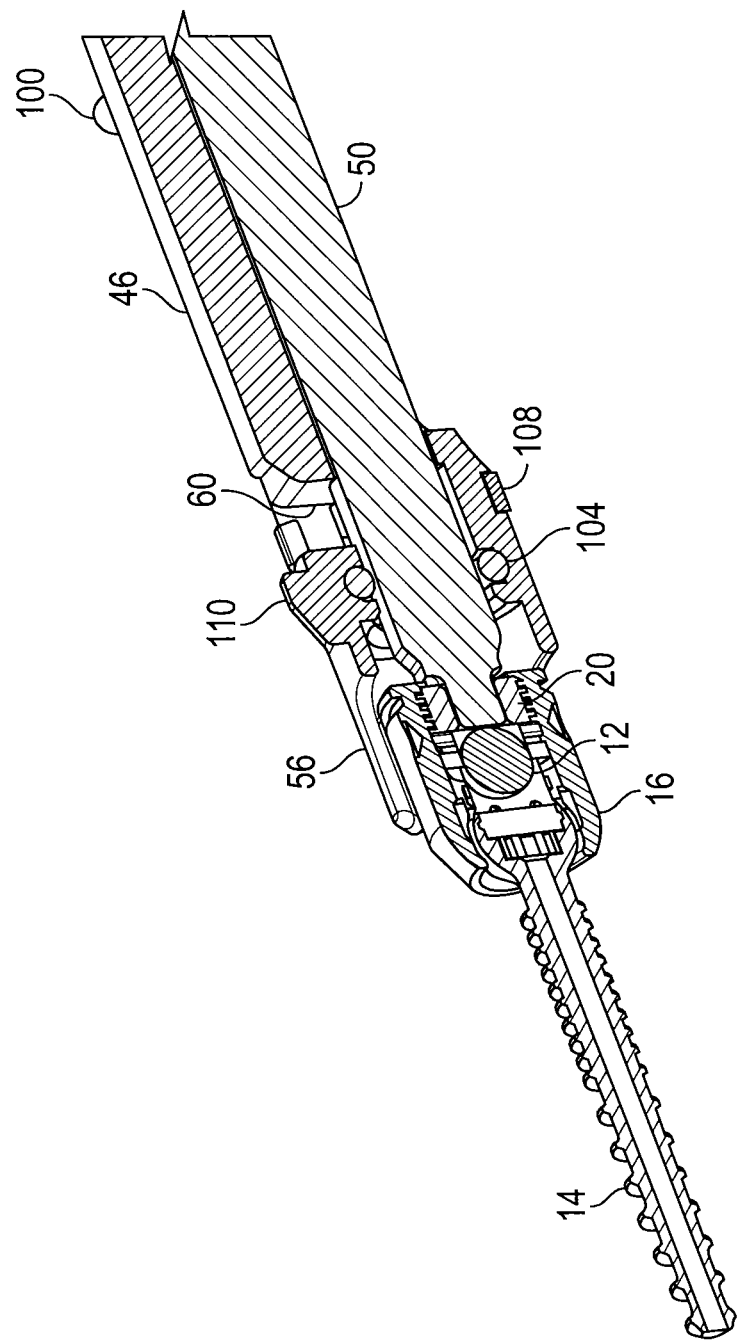
FIG. 27B is a partial, sectional view of the implant dispenser shown engaging the rod receiving head and shown with the driver and the implant disposed through the barrel and connected to the rod receiving head.

Referring to the illustrative embodiment of FIGS. 3-4, an implant dispenser 44 includes a barrel 46, a magazine 48 for storing implants and feeding same to the barrel 46, and a driver 50 slidably and rotatably disposed in the barrel 46 for mating engagement with the implants 20 disposed in the barrel 46. The barrel 46 has a sidewall 52, a proximal end 54, a distal end 56, and a longitudinal passage 58 extending through the barrel 46 from the proximal end 54 to the distal end 56. The distal end 56 of the barrel 46 may be configured to engage the rod receiving head 16 (FIGS. 1 and 27B). The barrel 46 further has a lateral passage 60 extending through the sidewall 52 of the barrel 46 and intersecting the longitudinal passage 58 adjacent the distal end 56.

Figure 23:
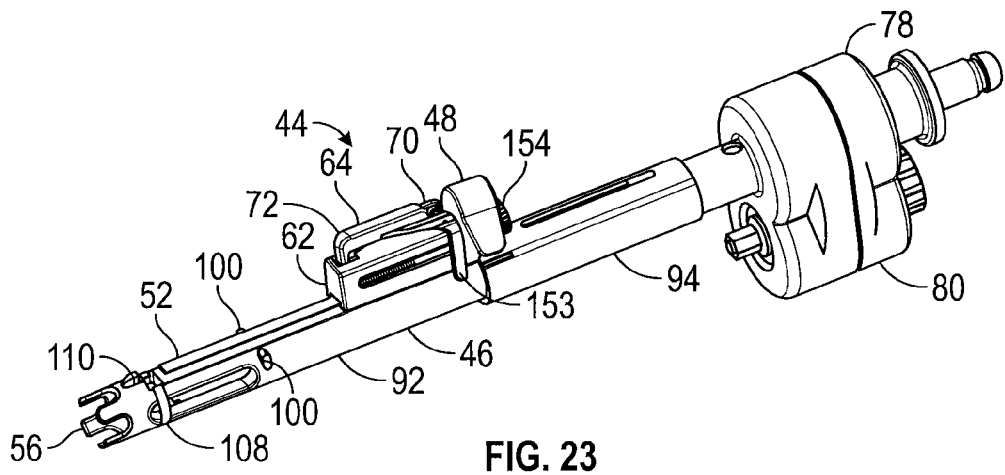
FIG. 23 is a perspective view of the implant dispenser with the magazine loaded with implants and the implant string removed from the magazine.

The magazine 48 has a housing 62 and a pusher member 64. The housing 62 defines a chamber 66 for receiving and storing the plurality of implants 20 and a slot 68 for discharging the implants 20 from the chamber 66. The pusher member 64 has a proximal end 70, a distal end 72, and is movably connected to the housing 62. The housing 62 is slidably connected to the sidewall 52 of the barrel 46 in a way that the housing 62 is movable between a retracted position (FIGS. 23 and 25) wherein the housing 62 is positioned away from the lateral passage 60 of the barrel 46 and an extended position (FIG. 24A) wherein the housing 62 is positioned so that the slot 68 of the housing 62 is aligned with the lateral passage 60 of the barrel 46 and the distal end 72 of the pusher member 64 is caused to push one of the implants 20 through the slot 68 and the lateral passage 60 and into the longitudinal passage 58 of the barrel 46.

Figure 26:
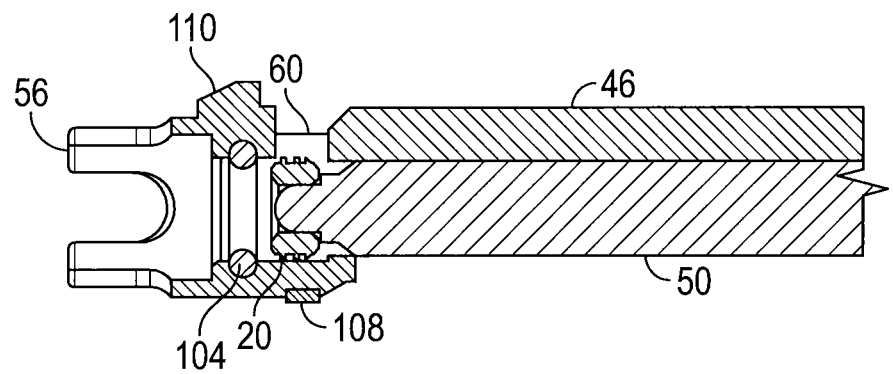
FIG. 26 is a partial, sectional view of the implant dispenser shown with the driver engaging the implant.

The driver 50 has a proximal end 74 and a distal end 76 engageable with the implants 20. The driver 50 is slidably and rotatably disposed in the longitudinal passage 58 of the barrel 46 such that the driver 50 is moveable between a retracted position (FIG. 24B) wherein the driver 50 is positioned to permit the implants 20 to be pushed into the longitudinal passage 58 through the lateral passage 60, an engaging position (FIG. 26) wherein the distal end 76 of the driver 50 is positioned to engage the implant 20 positioned within the longitudinal passage 58 of the barrel 46, and an extended position (FIG. 27B) wherein the driver 50 is positioned to transport the implant 20 to the distal end 56 of the barrel 46 where the driver 50 is rotatable to apply a rotational force to the implant 20 to thread the implant 20 to a rod receiving head 16.

In one embodiment, the implant dispenser 44 may include a drive mechanism 78 for controlling the rotation and the longitudinal position of the driver 50. The driver mechanism 78 may comprise a gearbox 80 and a power driver 82 operably connected to the gearbox 80. The gearbox 80 may be any type of gearbox suitable for controlling the torque applied to the implants 20 In one embodiment, the gearbox 80 may include a knob 84 for adjusting the torque placed on the implant 20 by the power driver 82. The power driver 82 may be configured to be handheld and include a first button 86 for activating and de-activating the power driver 82, a second button 88 to cause the driver 50 to rotate in a first direction, and a third button 90 to cause the driver 50 to rotate in a second direction opposite that of the first direction. In one embodiment, the power driver 82 may be powered via a battery pack (not shown). However, it will be appreciated that the power driver 82 may be powered by a variety of sources, including electric, hydraulic, and pneumatic (not shown).

As illustrated in FIG. 4, the drive mechanism 78 may be connected to the proximal end 74 of the driver 50 in a way to cause the driver 50 to rotate when the drive mechanism 78 is activated. The drive mechanism 78 may also be connected to the proximal end 54 of the barrel 46 in a way that the drive mechanism 78 and the driver 50 are movable together longitudinally relative to the barrel 46 for moving the driver 50 the retracted position, the engaging position, and the extended position. In one embodiment, the gearbox 80 may have a housing portion 81*a* with a tubular extension 81*b*. The tubular extension 81*b* may be slidably inserted into the proximal end 54 of the barrel 46 and connected thereto with a pair of tabs 91 that are slidably positioned in a pair of elongated slots (to be described in further detail below) provided in the proximal end 54 of the barrel 46 The drive mechanism 78 may further include a bushing 93 positioned between the tubular extension 81*b* and the driver 50 to connect the tubular extension 81*b* and the driver 50. The bushing 93 may have a flange 93*a* for supporting one end of a spring 95. As will be discussed below, the spring 95 is supported in the barrel 46 so as to bias the driver 50 in the retracted position.

Power drivers of the general type shown at 82 may be adapted to support and drive tool carriers of a variety of alternative kinds, for example carriers or chucks for drills, reamers, wire drivers, and sagittal, oscillating or reciprocating saws. In the embodiment shown, for the sake of example, the power driver 82 is shown as a tool capable of driving gearbox 80.

Referring now to FIGS. 3-12, in one embodiment the barrel 46 includes a barrel base 92 and a barrel sleeve 94. As shown in FIGS. 5-7, the barrel base 92 includes a proximal end 96, a distal end 98 defining the distal end 56 of the barrel 46, and at least one bumper member 100. The barrel base 92 is generally tubular so as to define a portion of the longitudinal passage 58 of the barrel 46. The proximal end 96 of the barrel base 92 is connected to the barrel sleeve 94 in a suitable manner, such as by welding.

The distal end 98 of the barrel base 92 is configured to engage the rod receiving head 16 (FIGS. 1 and 27B) so that the implant dispenser 44 may be used to apply a counter-force to the rod receiving head 16 in a manner to be discussed below. The distal end 98 of the barrel base 92 includes an opening 102 defining the lateral passage 60 and a retaining member 104 (FIGS. 4, 24B, 26, and 27B). The opening 102 is generally shaped to correspond with the shape of the implants 20, and thus permit the implants 20 to pass through the opening 102. In an embodiment, the opening 102 is rectangular, however, the opening 102 may be any shape as long as it is constructed to achieve the inventive concepts described herein.

The retaining member 104 is disposed in the longitudinal passage 58 of the barrel 46 distally of the lateral passage 60. The retaining member 104 supports the implant 20 after the implant 20 has been positioned in the longitudinal passage 58 with the driver 50 is in the retracted position. In one embodiment, the retaining member 104 is an elastic ring sized to permit passage of the implant 20 to the distal end 98 of the barrel base 92 when the driver 50 is moved to the extended position.

The distal end 98 of the barrel base 92 may include an annular groove 106 to allow for placement of a snap ring 108 (FIG. 10) around the annular groove 106. The snap ring 108 is resilient and includes a pair of ends 109*a* and 109*b* spaced apart in a way to prevent the implants 20 from entering into the barrel base 92 before the implants 20 are pushed past the end 109a and 109b through the slot 68 and the lateral passage 60 by the pusher member 64. The distal end 98 of the barrel base 92 may further include a stopper member 110 positioned in such a way that when the magazine 48 slides along the sidewall 52 of the barrel 46 towards the distal end 98 of the barrel base 92, the magazine 48 will contact the stopper member 110 and will be prevented from moving further towards the distal end 98 of the barrel base 92. The barrel base 92 may include a rail 111 extending from the proximal end 96 to the opening 102 for slidingly supporting the magazine 48 on the barrel base 92. In one embodiment, the distal end 98 of the barrel base 92 includes at least one elongated slot 112 positioned to allow for viewing of the driver 50 in the longitudinal passage 58 of the barrel 46.

The bumper members 100 are positioned on the barrel base 92 between the proximal end 96 of the barrel base 92 and the distal end 98 of the barrel base 92 in such a location that when the proximal ends 70 of the pusher member 64 contact the bumper members 100, the distal end 72 of the pusher member 64 is moved to cause one of the implants 20 to move past the snap ring 108, through the slot 68 of the chamber 66 and the lateral passage 60, and into the longitudinal passage 58 of the barrel 46.

Figure 11:
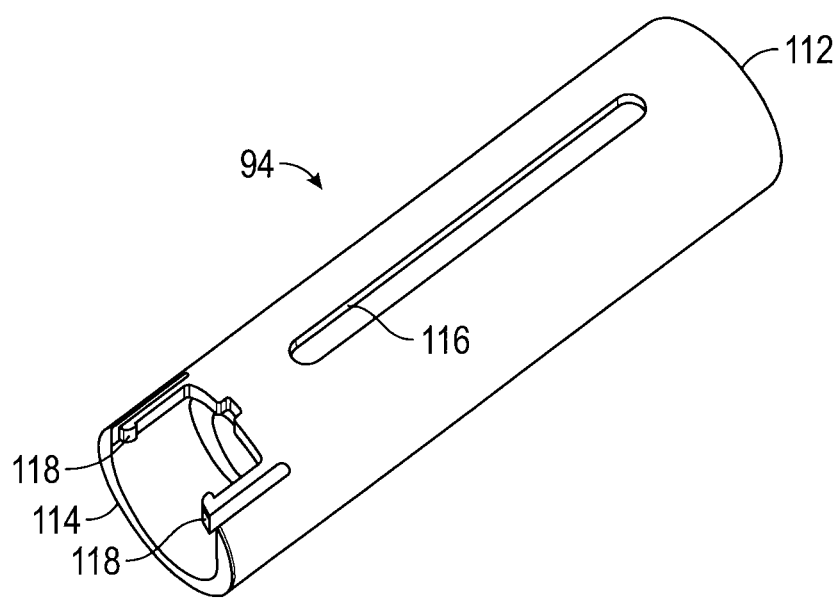
FIG. 11 is a perspective view of a barrel sleeve of the implant dispenser.
Figure 12:
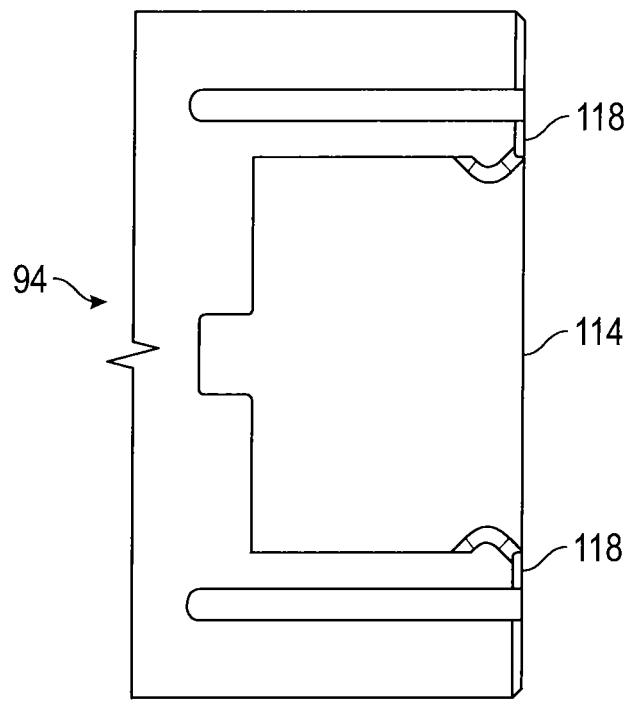
FIG. 12 is a top plan view of a portion of the barrel sleeve of FIG. 11.
Figure 13:
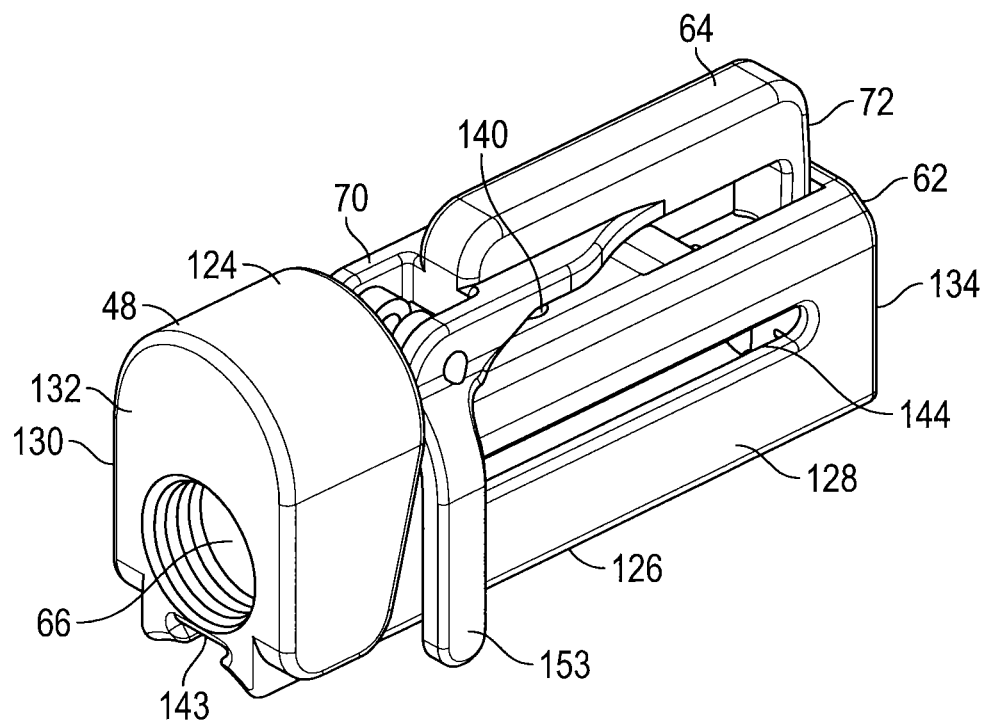
FIG. 13 is a perspective view of combination of a magazine and a pusher member.
Figure 14:
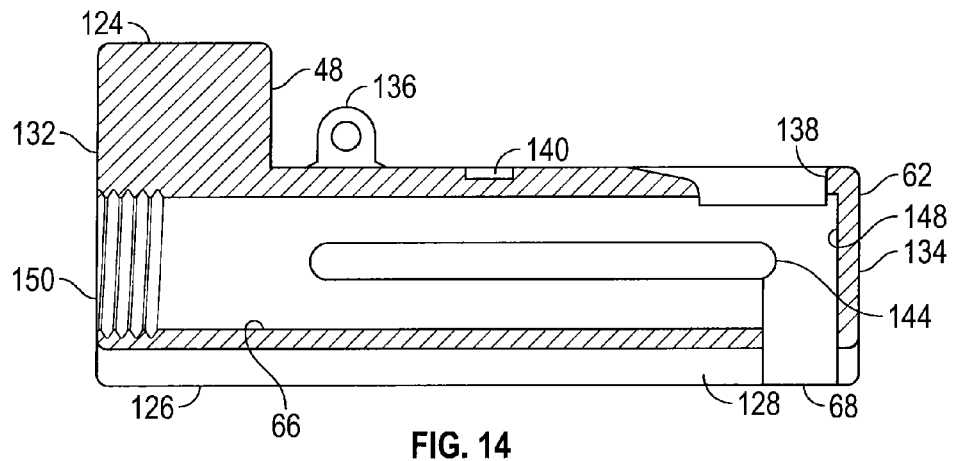
FIG. 14 is a sectional view of a housing of the magazine of FIG. 13.
Figure 15:
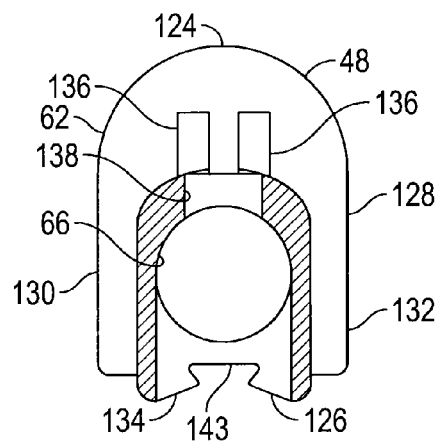
FIG. 15 is a cross sectional view taken along line 15-15 of FIG. 13 with a pusher member removed for clarity.
Figure 16:
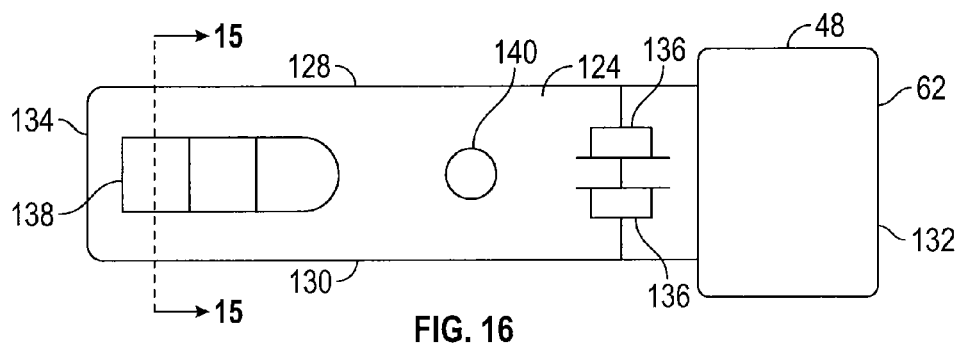
FIG. 16 is a top plan view of the housing of the magazine of FIG. 13.

Referring now to FIGS. 4 and 11-12, the barrel sleeve 94 includes a proximal end 112 and a distal end 114 connected to the proximal end 96 of the barrel base 92. The barrel sleeve 94 is generally tubular so as to define a portion of the longitudinal passage 58 of the barrel 46. The proximal end 112 of the barrel sleeve 94 defines the proximal end 54 of the barrel 46. The barrel sleeve 94 may further include a pair of elongated slots 116 (FIGS. 4 and 11) to facilitate connection with the drive mechanism 78. In particular, the elongated slots 116 slidingly receive the tabs 91 of the drive mechanism 78 in a way that the drive mechanism 78 and the driver 50 are slidable relative to the barrel sleeve 94. The spring 95 is positioned between the flange 93a of the bushing 93 and the distal end 114 of the barrel sleeve 94

As best shown in FIG. 12, the distal end 114 of the barrel sleeve 94 includes a pair of prongs 118. The prongs 118 are spaced apart to receive a portion of the rail 111 of the barrel base 92 there between and configured to resiliently grasp the housing 62 of the magazine 48 when the housing 62 is in the retracted position. A force may be applied on the housing 62 to remove the housing 62 from the grasp of the prongs 118 to allow sliding of the housing 62 along the sidewall 52 of the barrel 46.

Referring now to FIGS. 13-16 and as described above, the magazine 48 includes the housing 62 and the pusher member 64. The housing 62 defines the chamber 66 which is configured to receive the implants 20. The housing 62 has a top 124, a bottom 126, a first side 128, a second side 130, a proximal end 132, and a distal end 134. The top 124 of the housing 62 includes a pusher connector 136 and an opening 138. The pusher connector 136 provides a location for connection of the pusher member 64 to the housing 62. The pusher connector 136 may be positioned adjacent the proximal end 132 of the housing 62 while the opening 138 of the top 124 of the housing 62 is adjacent the distal end 134 of the housing 62 to allow the distal end 72 of the pusher member 64 to contact the distal most one of the implants 20 in the chamber 66. The top 124 of the housing 62 may further be provided with a recess 140 for placement of a spring 142 between the top 124 of the housing 62 and the pusher member 64 to bias the pusher member 64 in the retracted position.

The bottom 126 of the housing 62 includes a groove 143 which is configured to receive the rail 111 of the barrel base 92 to permit the housing 62 to slide along the sidewall 52 of the barrel 46. The bottom 126 of the housing 62 may include a pair of recesses 145 (only one visible in FIG. 3) configured to receive the prongs 118 of the barrel sleeve 94 when the housing 62 is in the retracted position. In one embodiment, one or both of the first side 128 of the housing 62 and the second side 130 of the housing 62 may be provided with an elongated slot 144 which allows for viewing of the caps 20 in the chamber 66.

The housing 62 may be configured to hold the implants 20 in a stack oriented in a substantially parallel relationship to the longitudinal passage 58 of the barrel 46. The slot 68 of the chamber 66 of the housing 62 is alignable with the lateral passage 60 of the barrel 46 so that the distal most one of the implants 20 is movable from the chamber 66 of the housing 62, through the slot 68, and through the lateral passage 60 of the barrel 46 in a way that one of the implants 20 is positioned in the longitudinal passage 58 of the barrel 46. In one embodiment, the proximal end 132 of the housing 62 may be provided with a threaded opening 150 in communication with the chamber 66.

In one embodiment, the pusher member 64 of the magazine 48 may be pivotally connected to the pusher connector 136 of the housing 62. The proximal end 70 of the pusher member 64 may include a pair of prongs 153 configured to contact the bumper members 100 of the barrel base 92 when the housing 62 is moved to the extended position in a way that the pusher member 64 is moved to cause the distal end 72 of the pusher member 64 to extend through the opening 138 of the top 124 of the housing 62 and into the chamber 66 to push one of the implants 20 through the slot 68 and the lateral passage 60 of the barrel 46. As discussed above, the spring 142 may be placed in between the top 124 of the housing 62 and the pusher member 64 to bias the pusher member 64 in the retracted position and thereby cause the pusher member 64 to exit the opening 138 of the top 124 of the housing 62, which allows for another implant 20 to move towards the distal end 148 of the chamber 66 by gravity or spring force.

Figure 17:
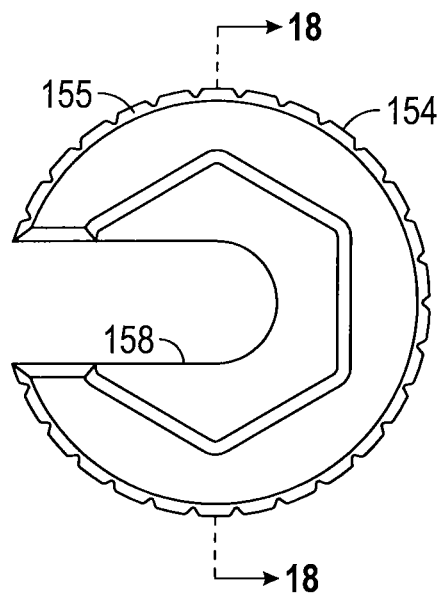
FIG. 17 is a top plan view of a magazine cap.
Figure 18:
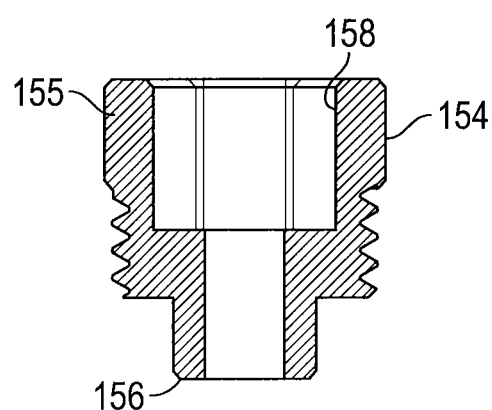
FIG. 18 is a sectional view taken along line 18-18 in FIG. 17.
Figure 21:
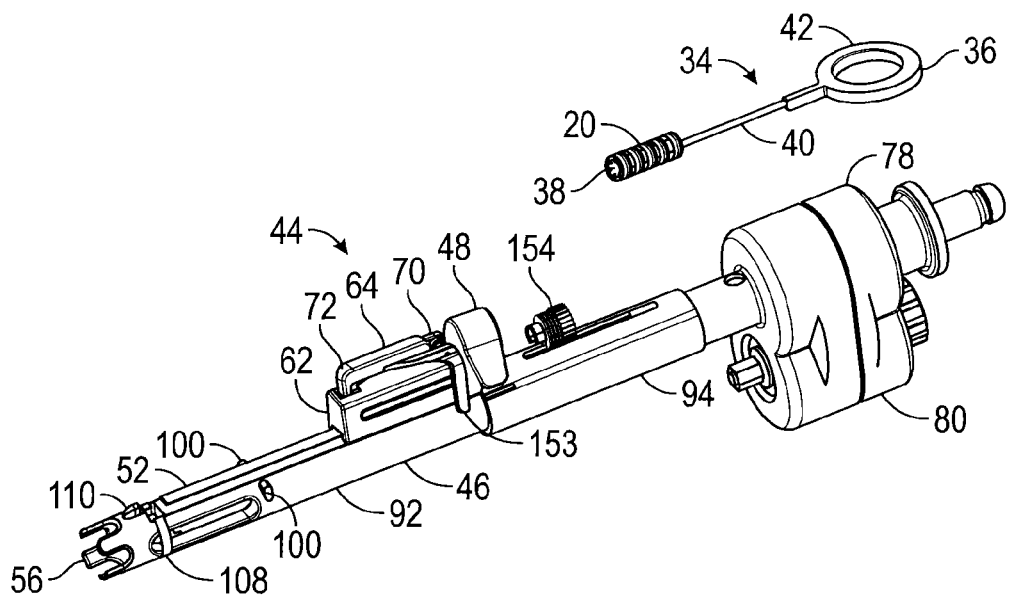
FIG. 21 is a perspective view of the implant dispenser and the implant string.
Figure 22:
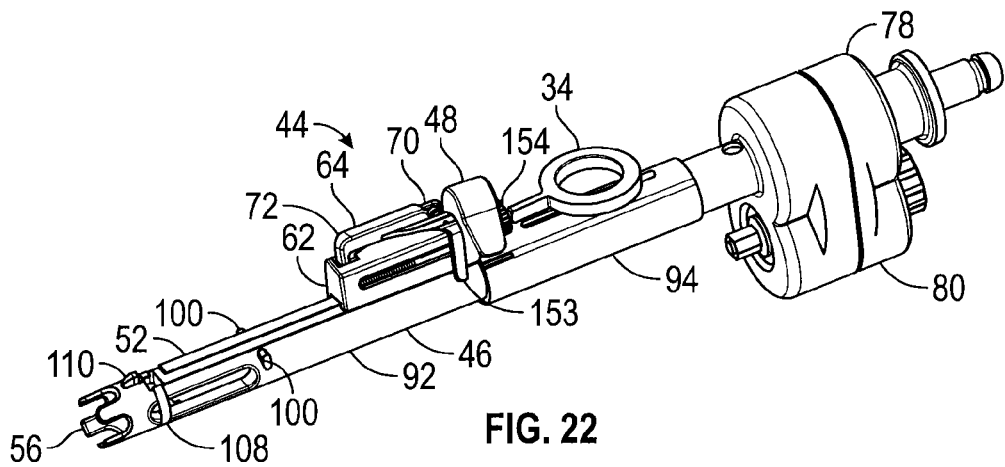
FIG. 22 is a perspective view of the implant dispenser with the magazine in a retracted position and with the implant string disposed in the magazine.

Referring now to FIGS. 17-18, the magazine 48 may include a magazine cap 154 threadingly received in the threaded opening 150 of the housing 62. The magazine cap 154 has a proximal end 155, a distal end 156, and a lateral recess 158 extending through the magazine cap 154 from the proximal end 155 to the distal end 156. The lateral recess 158 of the magazine cap 154 is sized such that the implant string 34 may be received by the lateral recess 158 of the magazine cap 154. Further, the lateral recess 158 is sized such that when the implant string 34 is loaded with implants 20 in the chamber 66, the implant string 34 may be pulled through the lateral recess 158 while the implants remain loaded in the chamber 66.

Referring now to FIGS. 19-20 and as previously discussed, the driver 50 has the proximal end 74 and the distal end 76. The driver 50 is generally cylindrical in shape so that it may be slidingly and rotatably moved in the longitudinal passage 58 of the barrel 46.

The proximal end 74 of the driver 50 is configured to be connected to the drive mechanism 78. To this end, the proximal end 74 may be key shaped for mating engagement with a hub of a gear 165 (FIG. 4) of the drive mechanism 78. In addition, the proximal end 74 may include a flange portion 166 for supporting the driver 50 relative to the drive mechanism 78. The distal end 76 of the driver 50 is configured to matingly engage the implants 20. The distal end 76 of the driver 50 is sized such that it may be disposed into the implant 20. The distal end 76 has a plurality of grooves 168. The grooves 168 of the distal end 76 of the driver 50 are formed such that the ridges 28 of the interior part 30 of the implant 20 may be received into the grooves 168 to provide a mating connection between the distal end 76 of the driver 50 and the implants 20.

The materials used to construct the implant dispenser 44 are those which have sufficient strength and biocompability, and are well known in the art for such devices. By way of example only, suitable materials include titanium, titanium alloys including Nitinol, and stainless steel. The implant string 34 may be a single use device and may be disposed of after use.

Operation

With particular reference to FIGS. 21-27B, an implant string 34 having the desired number of implants 20 is selected. To load the implant string 34 into the magazine 48, the user removes the magazine cap 154 from the housing 62 of the magazine 48. The implant string 34 is then inserted into the lateral recess 158 of the magazine cap 154 and then the implant string 34 and the magazine cap 154 are inserted into the chamber 66 of the housing 62. Once the magazine cap 154 has been secured to the housing 62, the loop 42 of the proximal end 36 of the implant string 34 may be pulled to remove the implant string 34 from the chamber 66 while the implants 20 are retained in the chamber 66 of the housing 62.

Figure 24A:
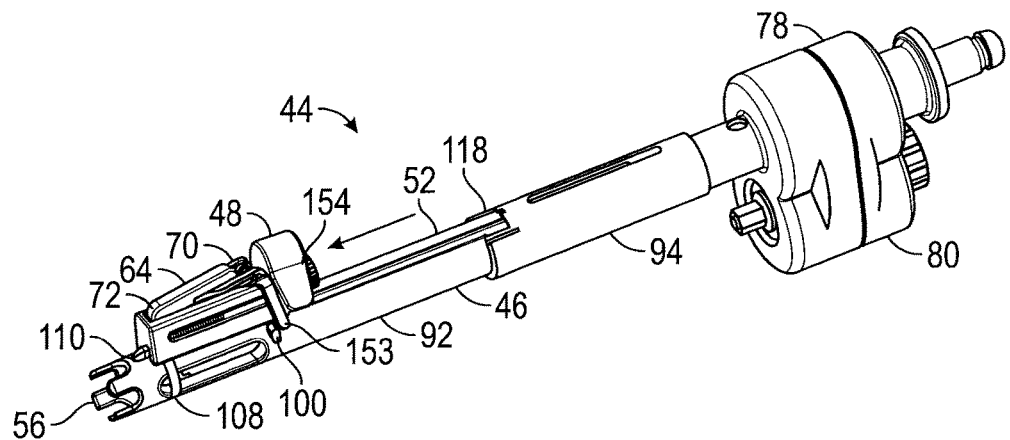
FIG. 24A is a perspective view of the implant dispenser shown with the magazine in an extended position.
Figure 24B:
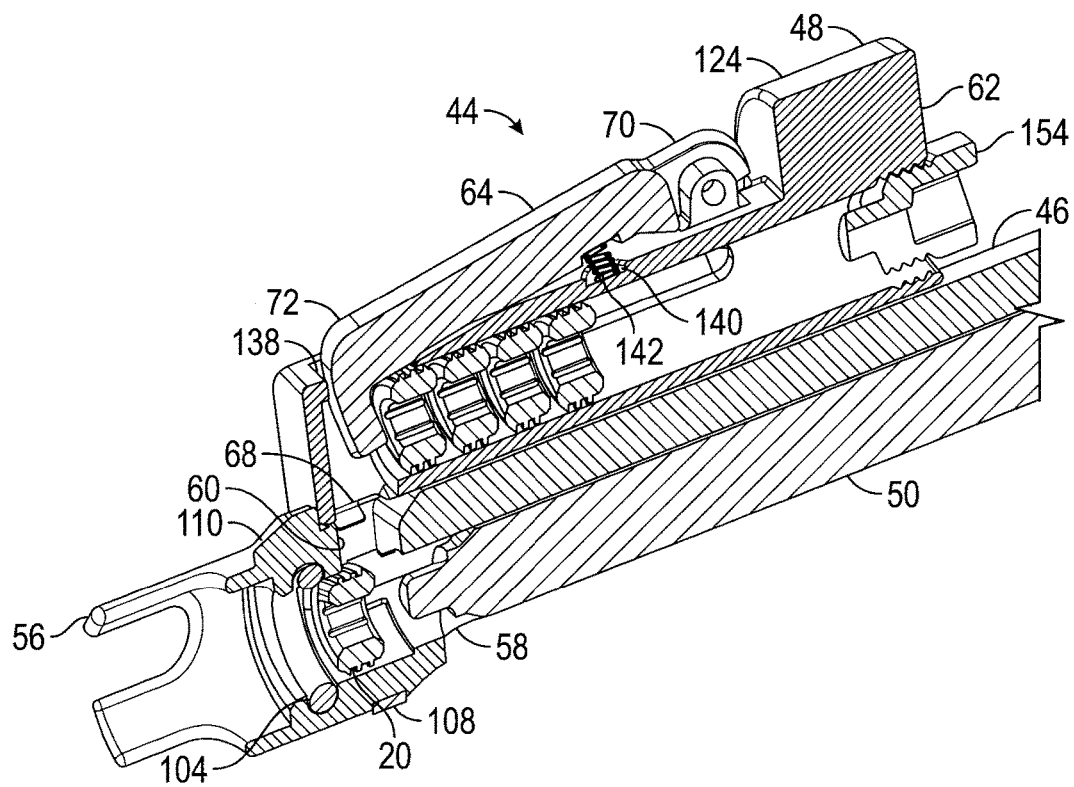
FIG. 24B is a partial, sectional view of the implant dispenser as shown in FIG. 24A.

With the implants 20 positioned in the chamber 66, the user may next slide the magazine 48 from the retracted position to the extended position (FIGS. 24A and 24B). To move the magazine 48 to the extended position, the magazine 48 will be slid along the sidewall 52 of the barrel 46 to cause the prongs 153 of the proximal end 70 of the pusher member 64 to contact the bumper members 100 of the barrel base 92. This contact causes the pusher member 64 to pivot and thereby cause the distal end 72 of the pusher member 64 to pass through the opening 138 of the top 124 of the housing 62 and push the distal most one of the implants 20 through the slot 68 of the housing 62, past the snap ring 108, through the lateral passage 60 of the barrel 46, and into the longitudinal passage 58 of the barrel 46.

Figure 25:
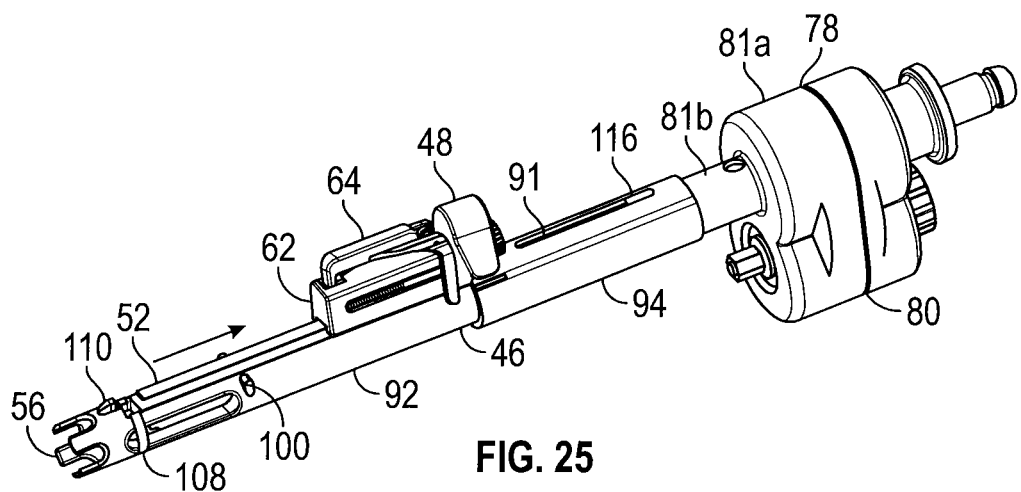
FIG. 25 is a perspective view of the implant dispenser shown with the magazine returned to the retracted position and a implant loaded into the barrel.

The implant 20 is now supported by the retaining member 104 of the barrel base 92 with the implant 20 positioned in the longitudinal passage 58 of the barrel 46 and the driver 50 in the retracted position. The magazine 48 may then be slid back along the sidewall 52 of the barrel 46 into the retracted position where the prongs 118 of the barrel sleeve 94 grasps the housing 62 of the magazine 48 to hold the magazine 48 in the retracted position (FIG. 25).

After the implant 20 is positioned in the longitudinal passage 58 of the barrel 46, the driver 50 may be moved from the retracted position (FIG. 25) to the engaging position (FIG. 26) by applying a force to the drive mechanism 78. With the implant 20 supported by both the retaining member 104 and the driver 50 in the engaging position, the user positions the distal end 56 of the barrel 46 over the rod receiving head 16 and the rod 12 positioned therein.

Next, the driver 50 is moved from the engaged position to the extended position (FIGS. 27A and 27B) by applying additional force to the drive mechanism 78 to cause the implant 20 to seat with the rod receiving head 16. The driver 50 is then caused to rotate to apply a rotational force to the implant 20 to thread the implant 20 to the rod receiving head 16. As the implant 20 is being threaded to the rod receiving head 16, an axial force may be applied to the barrel 46 so as to provide a rotational force to the rod receiving head 16 that is counter to the rotational force applied to the implant 20 by the driver 50.

Figure 28:
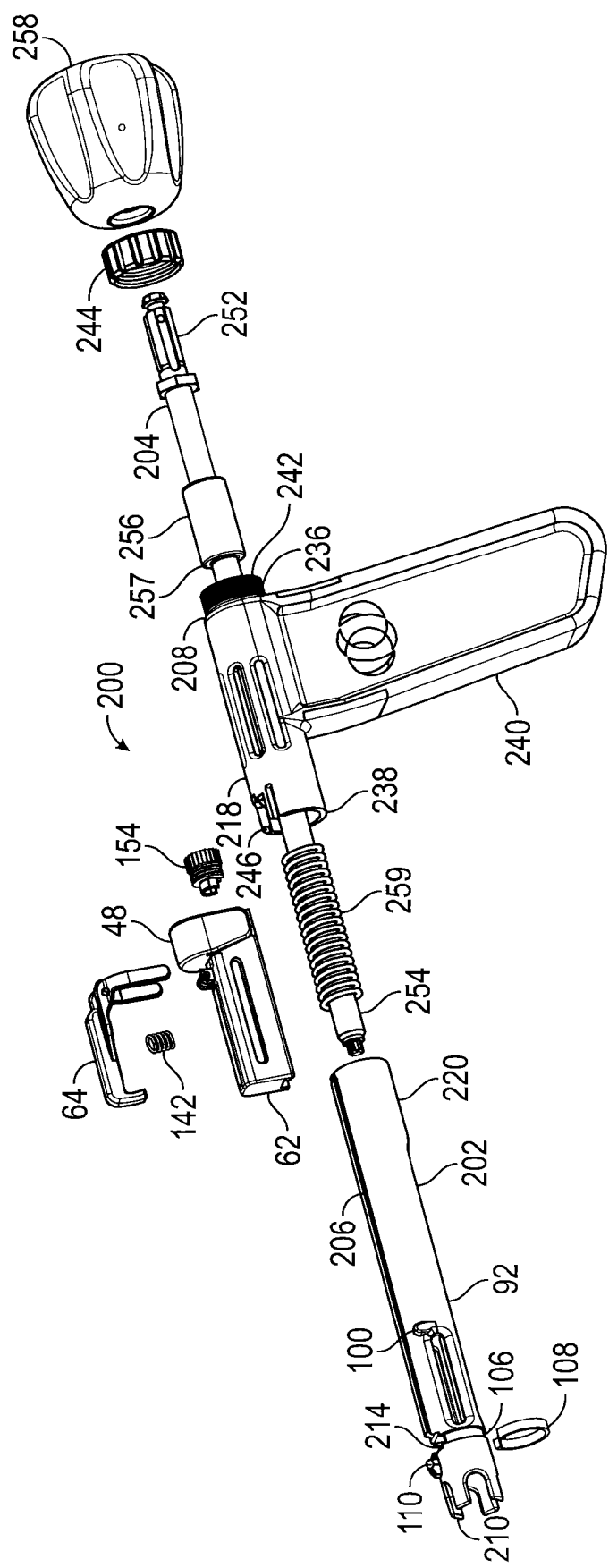
FIG. 28 is an exploded, perspective view of another embodiment of a implant dispenser constructed in accordance with the inventive concepts disclosed herein.
Figure 29:
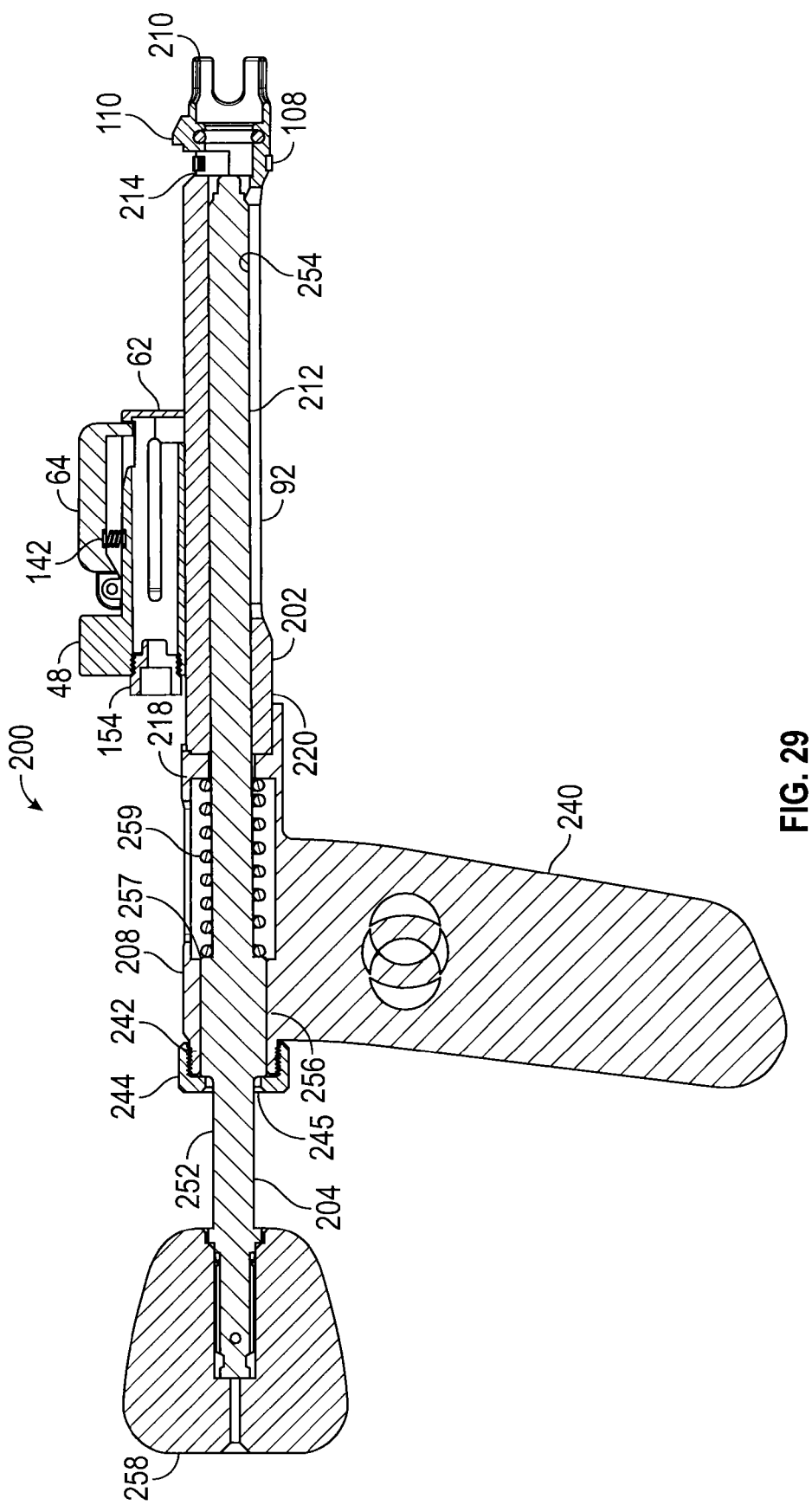
FIG. 29 is a sectional view of the implant dispenser of FIG. 28.
Figure 30:
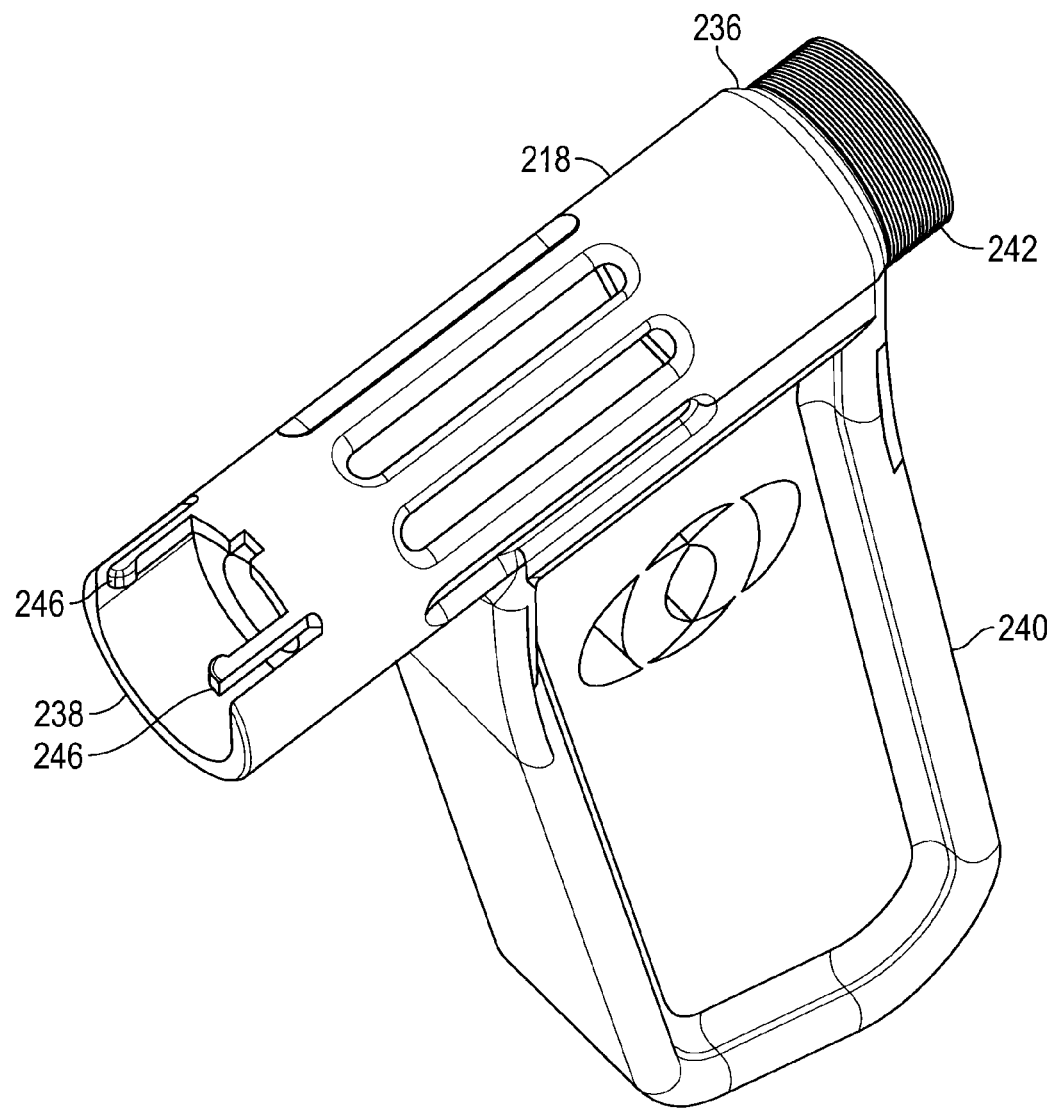
FIG. 30 is a perspective view of a barrel sleeve of the implant dispenser of FIG. 28.

Referring now to FIGS. 28-30, another embodiment of an implant dispenser 200 is illustrated. The implant dispenser 200 is similar to the implant dispenser 44, except as described below. Broadly, the implant dispenser 200 includes a barrel 202, the magazine 48 for storing implants and feeding same to the barrel 202, a driver 204 slidably and rotatably disposed in the barrel 202 for mating engagement with the implants 20 disposed in the barrel 202. As will be described below, the driver 204 is configured to be rotated manually.

The barrel 202 has a sidewall 206, a proximal end 208, a distal end 210, and a longitudinal passage 212 extending through the barrel 202 from the proximal end 208 to the distal end 210. The distal end 210 of the barrel 202 may be configured to engage the rod receiving head 16. The barrel 202 further has a lateral passage 214 extending through the sidewall 206 of the barrel 202 and intersecting the longitudinal passage 212 adjacent the distal end 210.

In one embodiment, the barrel 202 may include a barrel base, such as the barrel base 92 described above, and a barrel sleeve 218. The barrel sleeve 218 may include a proximal end 236, a distal end 238 connected to a proximal end 220 of the barrel base 92, and a handle 240. The barrel sleeve 218 is generally tubular so as to define a portion of the longitudinal passage 212 of the barrel 202. The proximal end 236 of the barrel sleeve 218 defines the proximal end 208 of the barrel 202. The proximal end 236 of the barrel sleeve 218 may include a threaded opening 242 for engagement with a barrel cap 244. The barrel cap 244 has a hole 245 for slidingly receiving a portion of the driver 204.

Like the barrel sleeve 94 described above, the distal end 238 of the barrel sleeve 218 includes a pair of prongs 246. The prongs 246 are configured to resiliently grasp the housing 62 of the magazine 48 when the housing 62 is in the retracted position.

The driver 204 has a proximal end 252 and the distal end 254 engageable with the implants 20. The driver 204 is generally cylindrical in shape so that it may be disposed in the longitudinal passage 212 of the barrel 202. The driver 204 is slidably and rotatably disposed in the longitudinal passage 212 of the barrel 202 such that the driver 204 is moveable between a retracted position wherein the driver 204 is positioned to permit the implants 20 to be pushed into the longitudinal passage 212 of the barrel through the lateral passage 214, an engaging position wherein the distal end 254 of the driver 204 is positioned to engage the implant 20 positioned within the longitudinal passage 212 of the barrel 202, and an extended position wherein the driver 204 is positioned to transport the implant 20 to the distal end 210 of the barrel 202.

The driver 204 includes an enlarged portion 256 defining a shoulder 257 for supporting a spring 259 between the shoulder 257 and the distal end 238 of the barrel sleeve 218. The spring 259 biases the driver 204 in the retracted position. The proximal end 252 of the driver 204 is configured to receive a knob 258. The knob 258 is connected to the proximal end 252 of the driver 204 to facilitate axial and rotational movement of the driver 204.

In use, the implant dispenser 200 functions in a manner similar to the implant dispenser 44. However, when the implant 20 has been positioned in the longitudinal passage 212 of the barrel 202, the driver 204 may be moved between the retracted position, the engaging position, and the extended position by manually pushing the knob 258 which causes the driver 204 to slide through the longitudinal passage 212. With the distal end 210 of the barrel 202 engaged to the rod receiving head 16, manual rotation of the knob 258 causes the driver 204 to rotate in a desired direction.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. An apparatus for dispensing a plurality of implants, the apparatus comprising:
    a barrel having a sidewall, a proximal end, a distal end, and a longitudinal passage extending through the barrel from the proximal end to the distal end, the barrel further having a lateral passage extending through the sidewall of the barrel and intersecting the longitudinal passage adjacent the distal end;
    a magazine having a housing defining a chamber for holding the plurality of implants, the housing connected to the barrel and the chamber of the housing configured to hold the plurality of implants in a stack oriented in a substantially parallel relationship to the longitudinal passage of the barrel, the housing having a slot alignable with the lateral passage of the barrel so that the implants are moveable from the chamber of the housing into the longitudinal passage of the barrel; and
    a driver having a proximal end and a distal end engageable with the implants, the driver slidably and rotatably disposed in the longitudinal passage of the barrel such that the driver is moveable between a retracted position wherein the driver is positioned to permit the implants to be pushed into the longitudinal passage through the lateral passage, an engaging position wherein the distal end of the driver is positioned to engage the implant positioned within the longitudinal passage of the barrel, and an extended position wherein the driver is positioned to transport the implant to the distal end of the barrel where the driver is rotatable to apply a rotational force to the implant.

2. The apparatus of claim 1, further comprising a drive mechanism connected to the proximal end of the driver to rotate the driver.

3. The apparatus of claim 1, further comprising a drive mechanism connected to the proximal end of the driver to rotate the driver and connected to the proximal end of the barrel in a way that the drive mechanism and the driver are movable longitudinally relative to the barrel.

4. The apparatus of claim 1, further comprising a retaining member disposed in the longitudinal passage of the barrel distally of the lateral passage to support the implant positioned in the longitudinal passage when the driver is in the retracted position and the engaging position while permitting passage of the implant to the distal end of the barrel when the driver is moved to the extended position.

5. The apparatus of claim 4, wherein the retaining member is elastic to permit passage of the implant to the distal end of the barrel when the driver is moved to the extended position.

6. The apparatus of claim 1, wherein the distal end of the barrel is configured to engage a rod receiving head to permit a rotational force to be applied to the rod receiving head that is counter to the rotational force applied to the implant by the driver when the distal end of the barrel is engaged with the rod receiving head.

7. An apparatus for dispensing a plurality of implants, the apparatus comprising:
    a barrel having a sidewall, a proximal end, a distal end, and a longitudinal passage extending through the barrel from the proximal end to the distal end, the barrel further having a lateral passage extending through the sidewall of the barrel and intersecting the longitudinal passage adjacent the distal end; and
    a magazine having a housing defining a chamber for holding the plurality of implants, the housing connected to the barrel and the chamber of the housing configured to hold the plurality of implants in a stack oriented in a substantially parallel relationship to the longitudinal passage of the barrel, the housing having a slot alignable with the lateral passage of the barrel so that the implants are moveable from the chamber of the housing into the longitudinal passage of the barrel in a way to be matingly engageable with a driver insertable in the longitudinal passage of the barrel where the driver is rotatable to apply a rotational force to one of the implants,
    wherein the housing is slidably connected to the sidewall of the barrel in a way that the housing is movable between a retracted position wherein the housing is positioned away from the lateral passage of the barrel and an extended position wherein the housing is positioned so that the slot of the housing is aligned with the lateral passage of the barrel.

8. The apparatus of claim 7, further comprising:
    a driver having a proximal end and a distal end engageable with the implants, the driver slidably and rotatably disposed in the longitudinal passage of the barrel such that the driver is moveable between a retracted position wherein the driver is positioned to permit the implants to be pushed into the longitudinal passage through the lateral passage, an engaging position wherein the distal end of the driver is positioned to engage the implant positioned within the longitudinal passage of the barrel, and an extended position wherein the driver is positioned to transport the implant to the distal end of the barrel where the driver is rotatable to apply a rotational force to the implant.

9. The apparatus of claim 8, further comprising a drive mechanism connected to the proximal end of the driver to rotate the driver.

10. The apparatus of claim 8, further comprising a drive mechanism connected to the proximal end of the driver to rotate the driver and connected to the proximal end of the barrel in a way that the drive mechanism and the driver are movable longitudinally relative to the barrel.

11. The apparatus of claim 8, further comprising a retaining member disposed in the longitudinal passage of the barrel distally of the lateral passage to support the implant positioned in the longitudinal passage when the driver is in the retracted position and the engaging position while permitting passage of the implant to the distal end of the barrel when the driver is moved to the extended position.

12. The apparatus of claim 11, wherein the retaining member is elastic to permit passage of the implant to the distal end of the barrel when the driver is moved to the extended position.

13. The apparatus of claim 7, wherein the distal end of the barrel is configured to engage a rod receiving head to permit a rotational force to be applied to the rod receiving head that is counter to the rotational force applied to the implant by the driver when the distal end of the barrel is engaged with the rod receiving head.

14. An apparatus for dispensing a plurality of implants, the apparatus comprising:
- a barrel having sidewall, a proximal end, a distal end, and a longitudinal passage extending through the barrel from the proximal end to the distal end, the barrel further having a lateral passage extending through the sidewall of the barrel and intersecting the longitudinal passage adjacent the distal end; and
- a magazine having a housing defining a chamber for holding the plurality of implants, the housing connected to the barrel and the chamber of the housing configured to hold the plurality of implants in a stack oriented in a substantially parallel relationship to the longitudinal passage of the barrel, the housing having a slot alignable with the lateral passage of the barrel so that the implants are moveable from the chamber of the housing into the longitudinal passage of the barrel in a way to be matingly engageable with a driver insertable in the longitudinal passage of the barrel where the driver is rotatable to apply a rotational force to one of the implants,
- wherein the magazine has a pusher member having a distal end and being movably connected to the housing, the housing being slidably connected to the sidewall of the barrel in a way that the housing is movable between a retracted position wherein the housing is positioned away from the lateral passage of the barrel and an extended position wherein the housing is positioned so that the slot of the housing is aligned with the lateral passage of the barrel and the distal end of the pusher member is caused to push one of the implants through the slot and the lateral passage and into the longitudinal passage of the barrel.

15. The apparatus of claim 14, wherein the pusher member has a proximal end, and wherein the barrel has at least one bumper member extending therefrom in a way that when the proximal end of the pusher member contacts the bumper member, the distal end of the pusher member is moved to cause one of the implants to move through the slot of the housing and the lateral passage and into the longitudinal passage of the barrel.

16. The apparatus of claim 14, further comprising:
- a driver having a proximal end and a distal end engageable with the implants, the driver slidably and rotatably disposed in the longitudinal passage of the barrel such that the driver is moveable between a retracted position wherein the driver is positioned to permit the implants to be pushed into the longitudinal passage through the lateral passage, an engaging position wherein the distal end of the driver is positioned to engage the implant positioned within the longitudinal passage of the barrel, and an extended position wherein the driver is positioned to transport the implant to the distal end of the barrel where the driver is rotatable to apply a rotational force to the implant.

17. The apparatus of claim 16, further comprising a drive mechanism connected to the proximal end of the driver to rotate the driver.

18. The apparatus of claim 16, further comprising a drive mechanism connected to the proximal end of the driver to rotate the driver and connected to the proximal end of the barrel in a way that the drive mechanism and the driver are movable longitudinally relative to the barrel.

19. The apparatus of claim 16, further comprising a retaining member disposed in the longitudinal passage of the barrel distally of the lateral passage to support the implant positioned in the longitudinal passage when the driver is in the retracted position and the engaging position while permitting passage of the implant to the distal end of the barrel when the driver is moved to the extended position.

20. The apparatus of claim 19, wherein the retaining member is elastic to permit passage of the implant to the distal end of the barrel when the driver is moved to the extended position.

* * * * *